United States Patent [19]

Archibald et al.

[11] Patent Number: 4,637,817

[45] Date of Patent: Jan. 20, 1987

[54] SEQUENCE VALVE FOR PIGGYBACK IV ADMINISTRATION WITH OCCLUSION FAILURE SENSING

[75] Inventors: G. Kent Archibald, White Bear Lake; Frank A. Slaker, New Brighton, both of Minn.

[73] Assignee: Minnesota Mining & Manufacturing Company, St. Paul, Minn.

[21] Appl. No.: 797,929

[22] Filed: Nov. 14, 1985

Related U.S. Application Data

[63] Continuation-in-part of Ser. No. 676,020, Nov. 29, 1984.

[51] Int. Cl.$^4$ .............................................. A61M 5/14
[52] U.S. Cl. ....................... 604/81; 604/250; 128/DIG. 13; 137/553; 137/595; 251/9; 251/68
[58] Field of Search ................. 604/80–83, 604/85, 249, 250, 245–248, 28–34, 258; 251/4–10,68; 128/DIG. 12, DIG. 13; 137/595, 553–555; 340/540, 679, 606; 200/61.42, 61.43

[56] References Cited

U.S. PATENT DOCUMENTS

| | | | |
|---|---|---|---|
| 3,601,124 | 8/1971 | Petree | 251/7 |
| 3,895,649 | 7/1975 | Ellis | 137/595 |
| 4,094,318 | 6/1978 | Burke et al. | 128/214 E |
| 4,114,617 | 9/1978 | Turner et al. | 128/214 R |
| 4,230,151 | 10/1980 | Jonsson | 137/595 |
| 4,236,880 | 12/1980 | Archibald | 417/478 |
| 4,265,240 | 5/1981 | Jenkins | 128/214 E |
| 4,316,460 | 2/1982 | Genese | 128/214 R |
| 4,324,238 | 4/1982 | Genese | 128/214 G |
| 4,391,598 | 7/1983 | Thompson | 604/65 |
| 4,397,642 | 8/1983 | Lamadrid | 604/245 |
| 4,425,116 | 1/1984 | Bilstad et al. | 604/34 |
| 4,430,074 | 2/1984 | Mooring | 604/49 |
| 4,451,255 | 5/1984 | Bujan et al. | 604/157 |
| 4,460,358 | 7/1984 | Somerville et al. | 604/250 |
| 4,484,599 | 11/1984 | Hanover et al. | 137/636.1 |
| 4,512,764 | 4/1985 | Wunsch | 604/80 |
| 4,533,347 | 8/1985 | Deckert | 604/81 |

FOREIGN PATENT DOCUMENTS 1130107 9/1956 France ................................ 251/9

*Primary Examiner*—Stephen C. Pellegrino
*Assistant Examiner*—Mario Costantino
*Attorney, Agent, or Firm*—Kinney & Lange

[57] ABSTRACT

A piggyback IV administration system uses a solenoid actuated sequence valve to control the flow of fluid from a pair of IV fluid sources to the inlet of an IV pump or controller. The sequence valve pinches off a first tube while allowing fluid to flow through the second tube and then, in response to a control signal, changes state so that the second tube is pinched off and fluid can flow through the first tube unimpeded. The sequence valve automatically senses conditions which indicate a failure of the sequence valve to occlude the second tube when the valve changes state.

27 Claims, 31 Drawing Figures

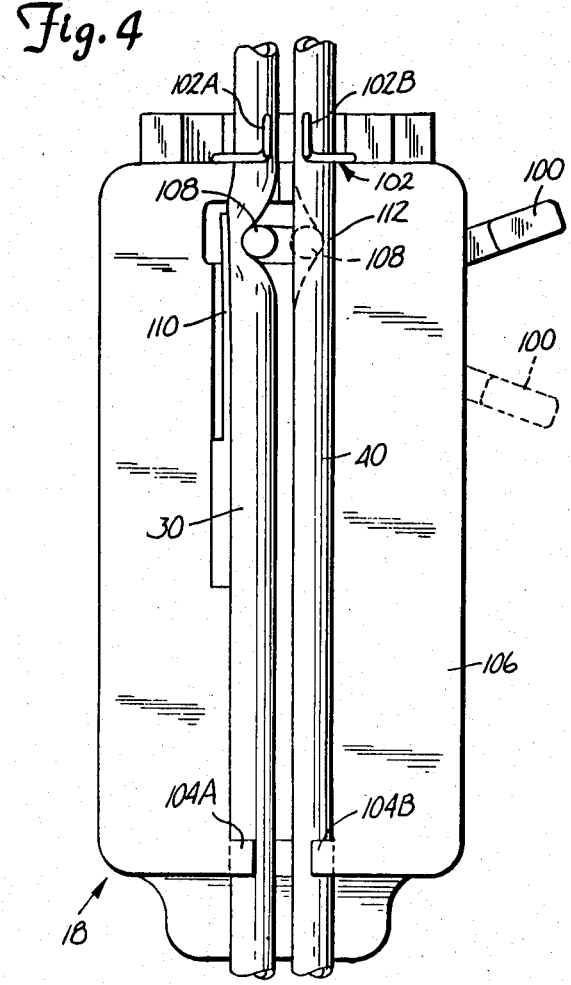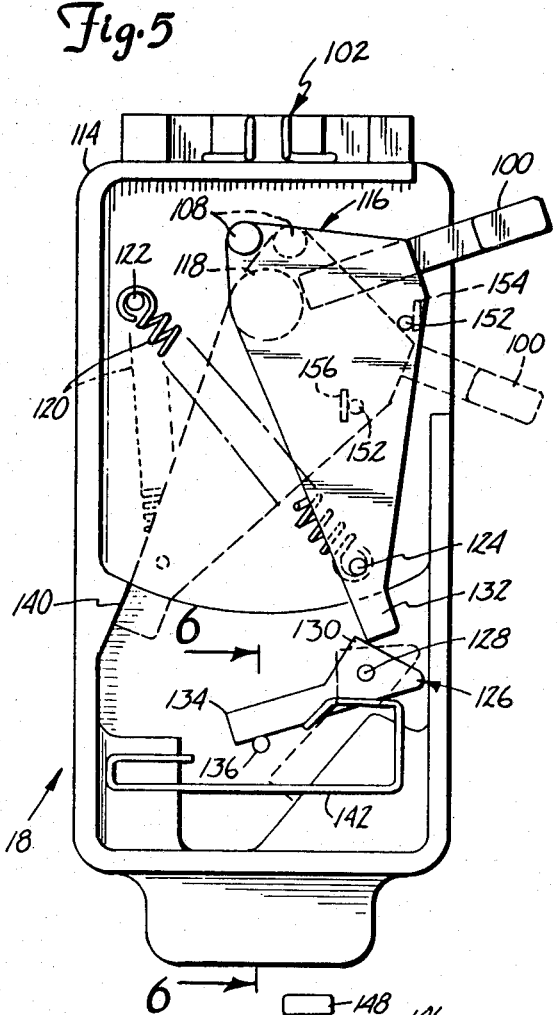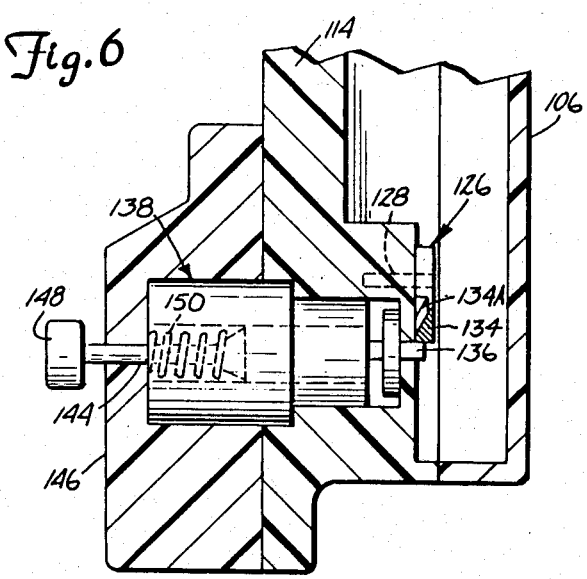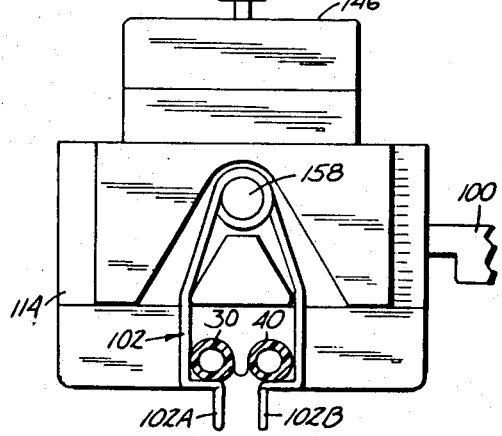

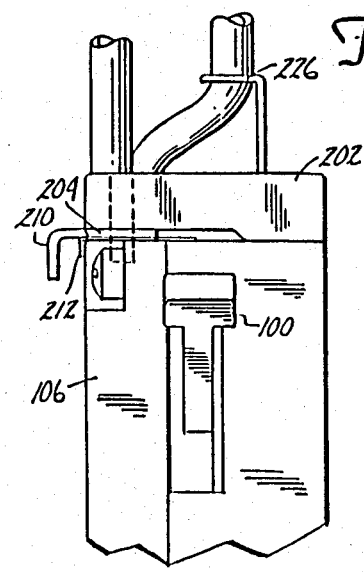
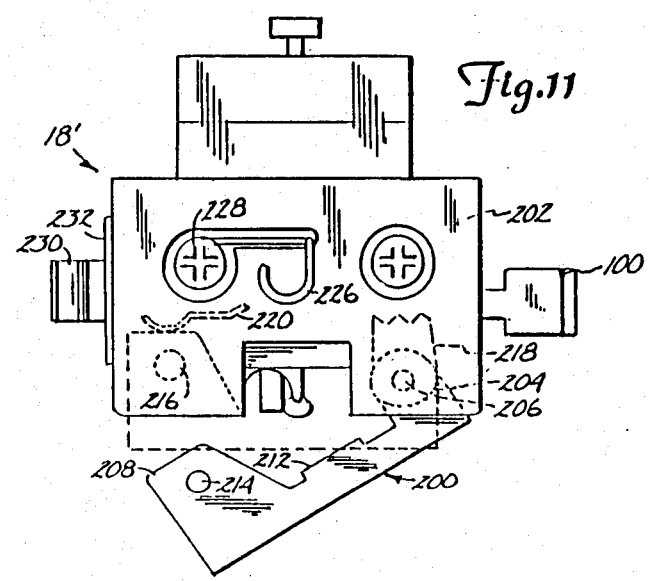
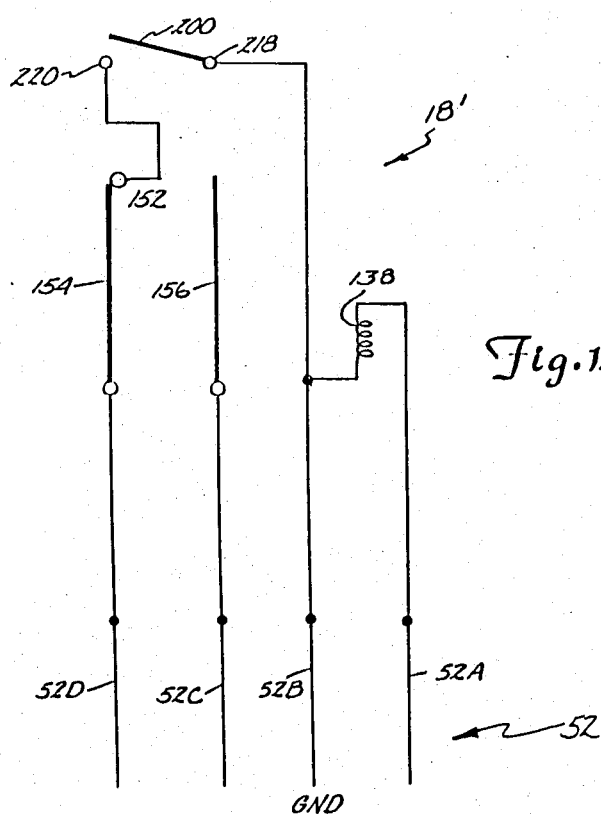

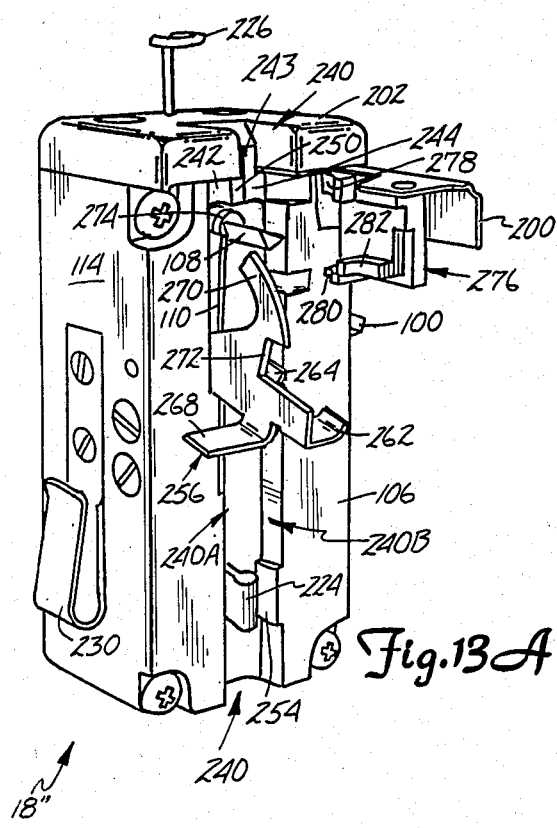

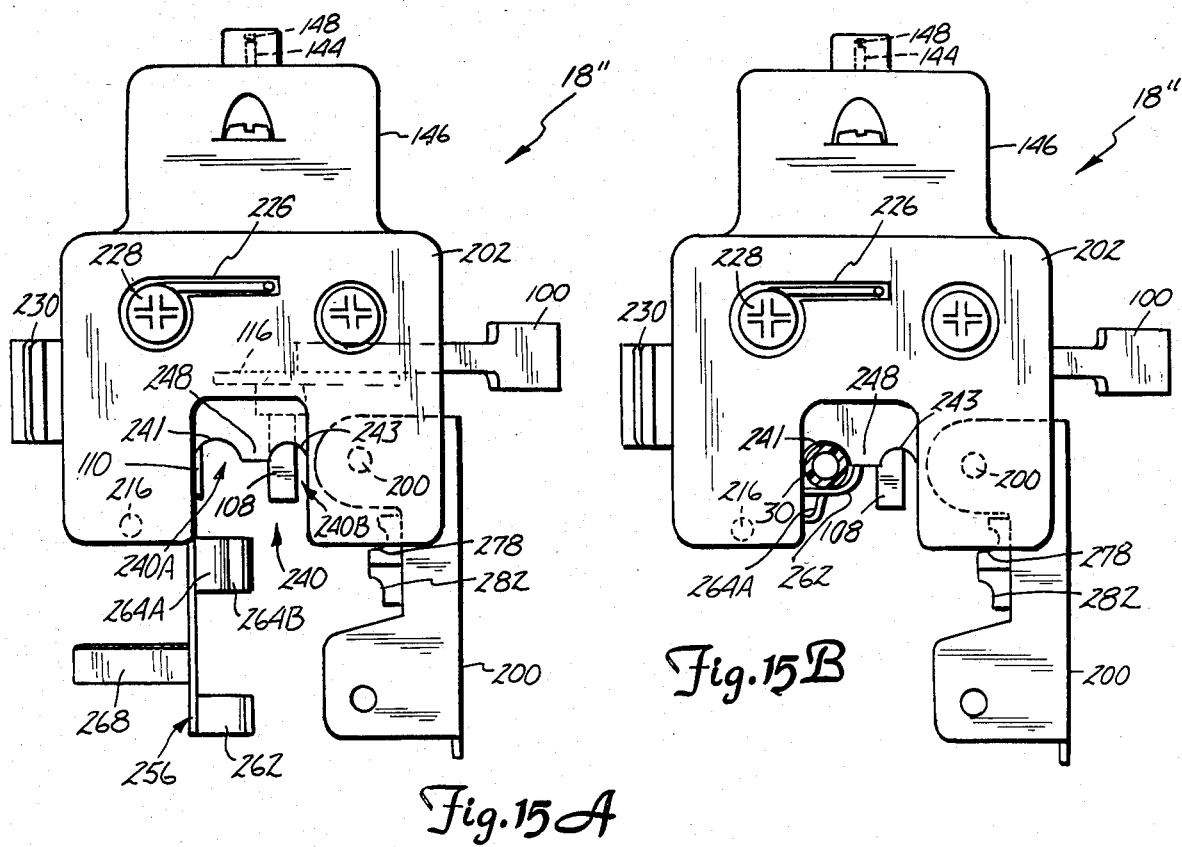
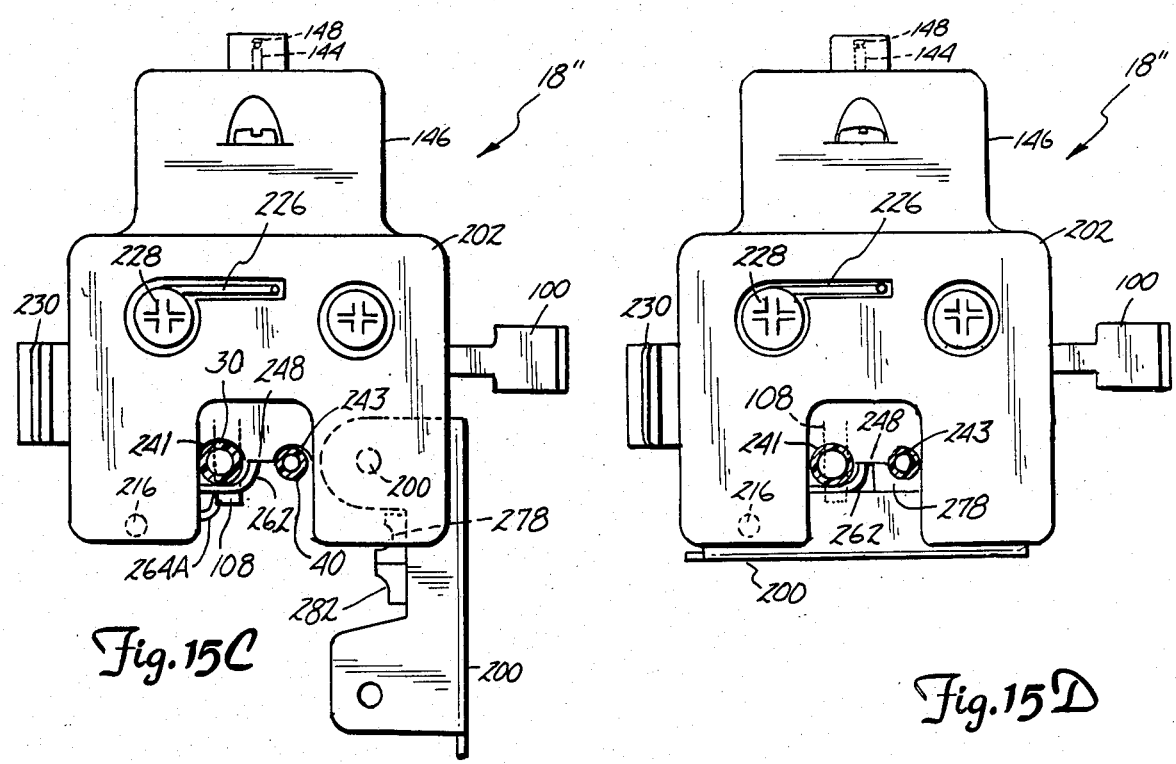

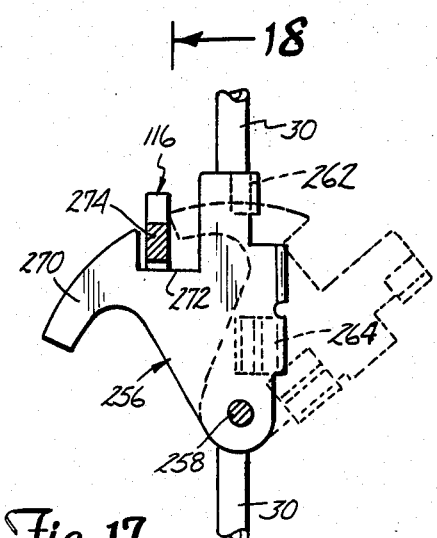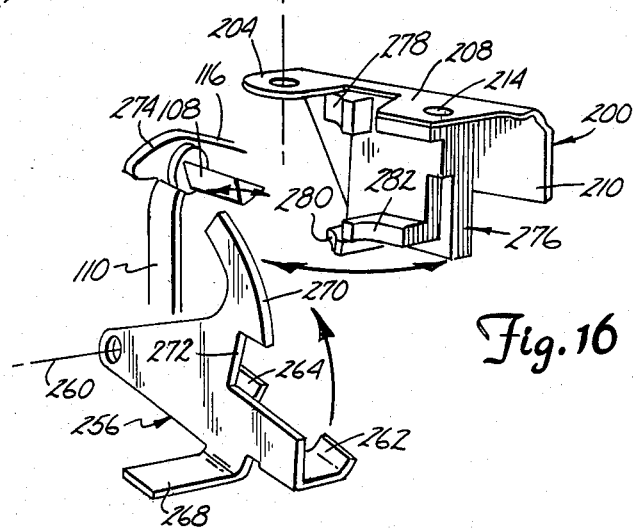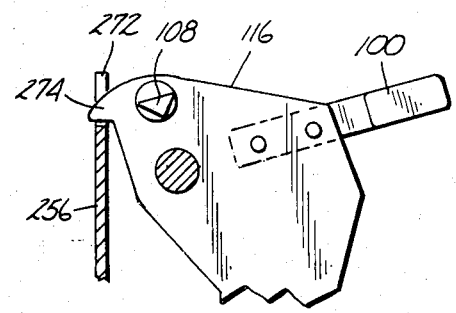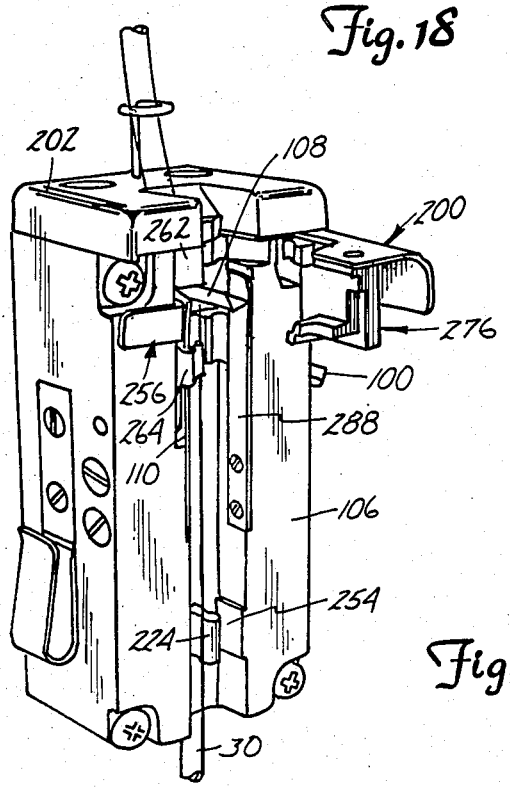

SEQUENCE VALVE FOR PIGGYBACK IV ADMINISTRATION WITH OCCLUSION FAILURE SENSING

REFERENCE TO COPENDING APPLICATION

This application is a continuation-in-part of application Ser. No. 676,020, filed Nov. 29, 1984.

Reference is made to a copending application Ser. No. 676,009 by G. K. Archibald entitled "Multiple Solution IV System" filed on Nov. 29, 1984 and assigned to the same assignee.

BACKGROUND OF THE INVENTION

1. Field of the Invention

The present invention relates to administration of intravenous (IV) fluid. In particular, the present invention is an IV administration system which supplies multiple IV solutions or medications at predetermined intervals to a patient.

2. Description of the Prior Art

It is quite common in IV therapy to give a patient a primary solution and one or more secondary solutions or medications. The secondary (or "piggyback") medication is usually given several times a day. An example is when a patient is on antibiotics. It is desirable to have an IV pump and a sequencing valve that administers the primary and secondary solutions sequentially.

In the past, there have been IV pump systems which allow two fluids to be administered. In these systems, the secondary medication is pumped until the secondary container goes empty, and then the pump switches to the primary fluid. An example of this type of system is shown in U.S. Pat. No. 4,451,255. This proves to be a substantial burden to hospital personnel, particularly where the secondary medication is required several times a day. With the prior art systems, the medical personnel must change secondary medication bags several times each day.

SUMMARY OF THE INVENTION

The present invention is an improved IV administration system which has a sequence valve which operates on two tubes which are connected between the inlet of an IV control device (e.g. a pump or controller) and a pair of sources of IV fluids. The sequence value is set to a first state in which the first tube is pinched off and the second tube is open. In response to a valve control signal, the sequence valve changes to a second state in which the second tube is pinched off and the first tube is open.

With the present invention, it is possible to provide multiple doses of the piggyback or secondary solution without having to change the secondary container. Since the secondary medication is intended to be provided to the patient only in limited doses, it is important that the patient not receive multiple doses at one time due to malfunction or improper setup of the sequence valve.

In the present invention, the sequence valve includes means for sensing a condition indicative of failure of the sequence valve to pinch off the second tube when the sequence valve changes to the second state. In one embodiment, the means for sensing a condition senses a rate of movement of the movable valve element (the occluder) which pinches off the second tube. If the rate of movement is not sufficiently high, this indicates that the occluder is not moving with sufficient momentum to fully pinch off the second tube, and results in an error condition being indicated.

In another embodiment, the means for sensing a condition senses the absence of the second tube from the sequence valve. This condition would also, of course, result in a failure to pinch off the second tube, and is indicated as an error condition.

BRIEF DESCRIPTION OF THE DRAWINGS

FIG. 4 is a front view of a first preferred embodiment of the sequence valve.

FIG. 5 is a front view of the sequence valve of FIG. 4 with the front cover removed.

FIG. 6 is a sectional view along section 6—6 of FIG. 5.

FIG. 7 is a top view of the valve of FIG. 4.

FIGS. 9 and 10 are partial left and right side views of the sequence valve of FIG. 8.

FIG. 11 is a top view of the sequence valve of FIG. 8 with the tube retainer pivoted to its open position.

FIG. 12 is an electrical schematic diagram of the sequence valve of FIG. 8.

FIGS. 13A–13D are perspective views showing the setup procedure for a third embodiment of the sequence valve.

FIGS. 15A–15D are top views, similar to FIGS. 13A–13D, respectively, of the sequence valve.

FIG. 16 is a perspective view showing positional relationships of the bell crank, control gate and tube retainer of the sequence valve of FIGS. 13A–15D.

FIG. 17 is a sectional view showing the positional relationships of the bell crank, control gate and tube retainer.

FIG. 18 is a sectional view along section 18—18 of FIG. 17.

FIG. 20 shows a perspective view of a fourth embodiment of the sequence valve.

DETAILED DESCRIPTION OF THE PREFERRED EMBODIMENTS

Figure 1:
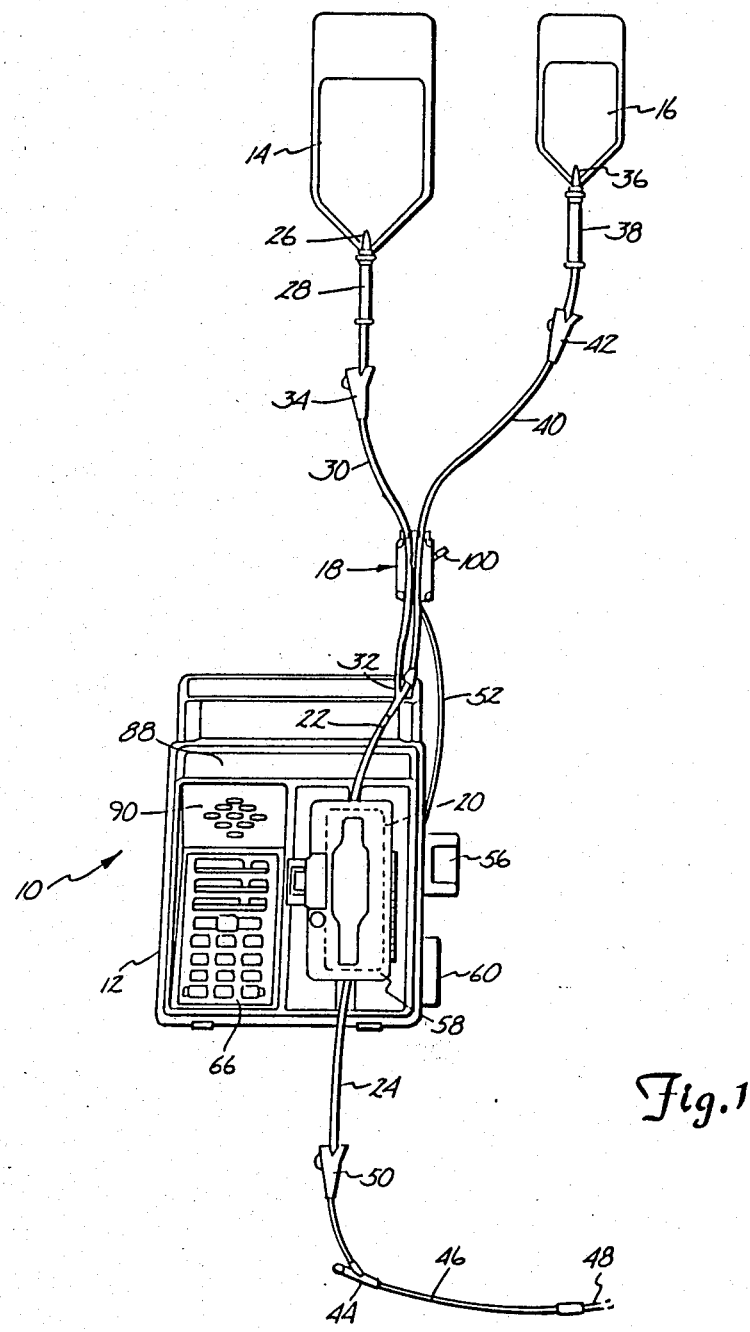
FIG. 1 is a partially schematic diagram of a preferred embodiment of the IV administration system using the sequence valve of the present invention.

In the preferred embodiment shown in FIG. 1, IV administration system 10 includes IV pump 12, which pumps fluid from primary solution bag 14 to secondary (or piggyback) solution bag 16, to a patient (not shown). Sequence valve 18 is connected between bags 14 and 16 and pump 12 to select one of the bags 14 and 16 for connection to pump 12.

In the particular embodiment shown in FIG. 1, pump 12 is an IV pump such as the AVI GUARDIAN 400 pump. Pumps of this general type (which are described in U.S. Pat. No. 4,236,880) use a disposable multiple rolling diaphragm pumping chamber 20 which is inserted into pump 12. Pumping chamber 20 has an inlet tubing 22 connected at its inlet end, and an outlet tubing 24 at its outlet end. A drive mechanism within pump 12 causes relative movement of two of the rolling diaphragms of pumping chamber 20 and the operation of two valves to cause fluid to be pumped from inlet tubing 22 through pumping chamber 20 and out through outlet tubing 24 to the patient.

In the embodiment shown in FIG. 1, disposable multiple rolling diaphragm pumping chamber 20, inlet tubing 22 and outlet tubing 24 form a part of a disposable IV administration set which also includes primary spike 26, primary drip chamber 28, primary tubing 30, proximal Y connector 32, primary roller clammp 34, secondary spike 26, secondary drip chamber 38, secondary tubing 40, secondary roller clamp 42, distal Y connector 44, distal tubing 46, needle 48, and distal roller clamp 50.

Primary spike 26 is inserted into the lower end of primary bag 14, and is connected to the upper end of primary drip chamber 28. The lower end of primary drip chamber 28 is connected by primary tubing 30 to one leg of proximal Y connector 32.

Similarly, secondary spike 36 is inserted into the lower end of secondary bag 16 and is connected to the upper end of secondary drip chamber 38. The lower end of secondary drip chamber 38 is connected through secondary tubing 40 to the second leg of proximal Y connector 32. The third leg of Y connector 32 is connected to inlet tubing 22.

Primary tubing 30 and secondary tubing 40 pass through sequence valve 18, and at least one (preferably primary tubing 30) supports sequence valve 18. In the preferred embodiment of the present invention, sequence valve 18 is a light-weight, solenoid actuated device which initially pinches off primary tubing 30 to prevent flow from primary bag 14 while permitting flow from secondary bag 16 to pumping chamber 20. In response to a valve control signal received from pump 12 through multiconductor cable 52, sequence valve 18 switches so that secondary tubing 40 is pinched off and primary tubing 30 is unobstructed. When secondary tubing 40 is unobstructed and primary tubing 30 is pinched off, secondary (piggyback) bag 16 is connected to inlet tubing 22, and pump 12 pumps the secondary medication from piggyback bag 16 to the patient. Conversely, when secondary tubing 40 is pinched off and primary tubing 30 is unobstructed, the primary solution is pumped from primary bag 14 to the patient by IV pump 12.

At the outlet end, outlet tubing 24 is connected through distal Y connector 44 to distal tubing 46. At the end of distal tubing 46 is needle 48, which is inserted into a vein of the patient. Distal Y connector 44 has another leg which is normally closed, but which allows the insertion of a syringe needle to introduce medication directly into distal tubing 46 as fluid is being pumped to the patient.

Roller clamps 34, 42 and 50 are used by medical personnel during the installation of the IV administration set into pump 12, during initial set-up, and during removal of the IV administration set.

Figure 2:
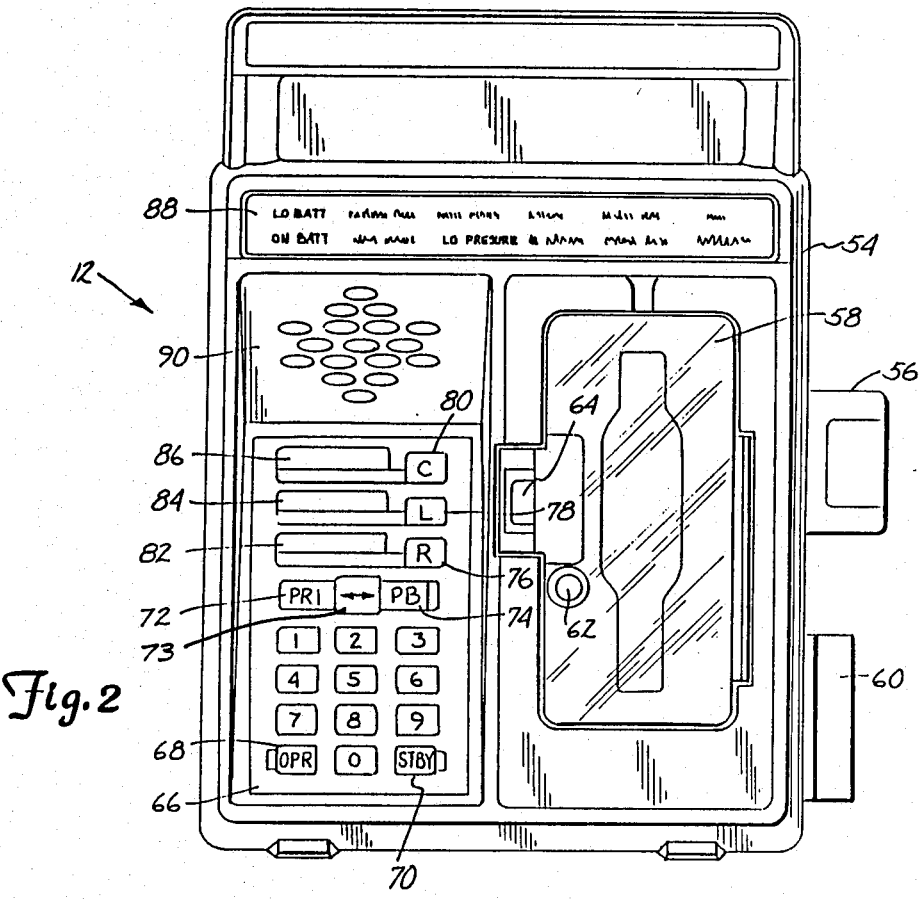
FIG. 2 is a front view of the IV pump of FIG. 1.

FIG. 2 shows a front view of pump 12. Pump 12 includes a housing 54 which contains the electrical control circuitry and the mechanical portions of the pump which interact with disposable pumping chamber 20. Pump 12 is supported on an IV stand or pole (not shown) by pole clamp 56. Door 58 covers a receptacle into which disposable pumping chamber 20 is inserted. In the embodiment shown in FIG. 2, the opening of door 58 requires operation of the three separate devices: load control handle 60, door lock 62, and door latch 64. During normal operation, when the IV administration set is installed with pumping chamber 20 within the receptacle of pump 12, door 58 is closed as shown in FIG. 2.

In the lower left corner of the front of pump 12 is control panel 66, which includes a keyboard formed by numerical key pads ("0" through ("9"), operate key pad (OPR) 68, standby key pad (STBY) 70, PRIMARY indicator 72, PRIMARY-PIGGYBACK toggle key pad 73, PIGGYBACK indicator 74, RATE key pad 76, volume limit (LIMIT) key pad 78, and volume infused clear (CLEAR) key pad 80. Control panel 66 also includes three digital displays: rate display 82, volume limit display 84, and volume infused display 86.

Pump 12 also includes indicator panel 88 (which provides visual indication of different error or alarm conditions), and audio alarm annunciator 90.

Figure 3:
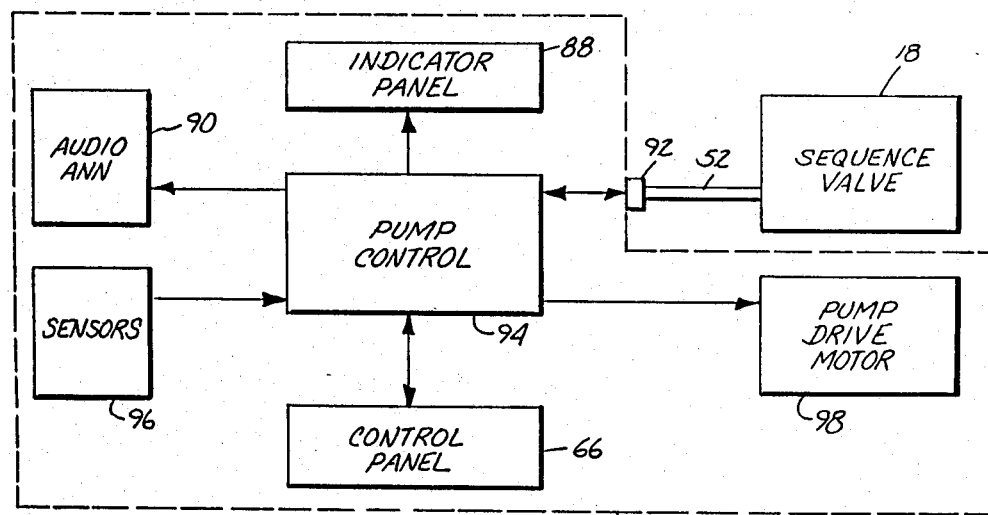
FIG. 3 is an electrical block diagram of the system of FIG. 1.

FIG. 3 is an electrical block diagram of pump 12 and sequence valve 18, which are connected together by multiconductor cable 52 and connector 92. Sequence valve 18 receives a valve control signal from pump 12, and provides a valve state signal, which indicates which fluid line (primary tubing 30 or secondary tubing 40) is occluded.

The operation of pump 12 is controlled by pump control 94, which in preferred embodiments includes a microcomputer, together with associated memory, timing and clock circuitry and appropriate interface circuitry. Pump control 94 receives input signals from control panel 66, from sensors 96 (which sense various operating conditions or parameters such as output pressure, air bubbles in the IV administration set, empty bags and opening of door 58), and from sequence valve 18. Pump control 94 provides outputs to displays 82, 84 and 86 of control panel 66, indicator panel 88, audio annunciator 90 and to pump drive motor 98. In addition, when sequence valve 18 is connected to pump 12 and a piggyback operation has been selected, pump control 94 provides the valve control signal to sequence valve 18.

Control panel 66 allows the medical personnel to "set up" an IV administration schedule so that predetermined volumes of the primary and secondary solutions are delivered at predetermined rates. Pump control 94 controls the operation of both sequence valve 18 and pump drive motor 98, so that it controls both the particular solution being pumped at any given time, and the rate at which the fluid is being pumped.

By depressing STBY key pad 70, the medical personnel places pump 12 in a standby mode. This allows changing or resetting of both rates and volume limits for both the primary and piggyback solutions. The primary solution rate is selected by depressing PRIMARY-PIGGYBACK toggle key pad 73 (toggling to the PRIMARY MODE) and then RATE key pad 76, followed by the keys representing the numerical value desired. The primary volume limits can then be set by pressing LIMIT key pad 78 and then using the numerical keys to enter the desired numerical limit for the primary solution.

For the piggyback or secondary solution PRIMARY-PIGGYBACK toggle key pad 73 is pressed to toggle to the PIGGYBACK mode. RATE key pad 76 is then pressed, followed by appropriate numerical keys to enter the piggyback rate. LIMIT key pad 78 is then depressed, followed by selected numerical key pads to set the piggyback volume limit.

Pump control 94 stores the rates and volume limits entered for both the primary solution and the piggyback solution. These stored values are used, together with an accumulated volume infused value in controlling sequence valve 18 as well as pump drive motor 98.

Sequence valve 18 of the present invention is a spring loaded, solenoid actuated device which initially occludes primary tubing 30 so that the secondary solution is pumped first. Sequence valve 18 is placed in this initial condition by inserting primary tubing 30 into one slot of sequence valve 18 and then cocking lever 100 so that primary tubing 30 is occluded. Secondary tubing 40 is then inserted into an adjacent slot alongside primary tubing 30 in sequence valve 18 as shown in FIG. 1.

Operation of pump 12 in the piggyback mode is initiated by depressing OPR key pad 68. Pump control 94 provides pump drive control signals to pump drive motor 98 which cause motor 98 to produce the pumping rate stored for the piggyback solution. As pump drive motor 98 is operated, pump control 94 maintains an accumulated value which represents the amount of secondary solution which has been pumped with sequence valve 18 in its initial setting. When that accumulated value reaches the piggyback volume limit stored by pump control 94, a valve control signal is produced which causes sequence valve 18 to change state. Sequence valve 18, in response to the valve control signal, occludes secondary tubing 40, and allows primary solution to flow through primary tubing 30, to inlet tubing 22. Upon receiving the signal from sequence valve 18 indicating that the change has been made, pump control 94 provides pump drive signals which cause pump drive motor 98 to operate at the pumping rate selected for the primary solution. Pump control 94 again maintains an accumulated value which represents the amount of primary solution which has been pumped. This value is displayed on volume infused display 86. When the accumulated value reaches the stored primary volume limit, pump control 94 halts operation of pump drive motor 98 and provides an indication through indicator panel 88 and audio annunciator 90 that both the piggyback and primary administration have been completed. At that point, the medical personnel responsible for the IV administraiton are required to intervene to set a new schedule of primary and piggyback rates and volume rates.

The present invention is advantageous because all of the medication for a single day or for several days can be stored in one large secondary bag 16, as opposed to much smaller secondary bags which run dry after each administration of that medication. For example, if a patient is to receive 50 milliliters of secondary medication four times a day, four bags would be required with the prior art systems, in which the switching from the secondary bag to the primary solution is determined by when the secondary bag is empty. With the system of the present invention, one 200 milliliter bag can be used for the entire day. Since a large or a small bag costs essentially the same, there is a cost saving just by virtue of the reduced number of bags. In addition, the system significantly reduces the amount of time which is required of medical personnel. It is not necessary to change the secondary bag 16 after each administration of medication, and in fact the present invention allows the secondary medication to be provided multiple times without a change in the secondary bag.

By use of pump control 94 within housing 54 of pump 12 to control operation of both pump 12 and sequence valve 18, the size, weight, complexity and cost of sequence valve 18 are significantly reduced. As a result, sequence valve 18 can be suspended from the tubing (e.g. primary tubing 30) rather than requiring separate clamping to a pole. This makes sequence valve 18 simpler and easier to use, and makes it portable so that sequence valve 18 can be moved wherever pump 12 is moved.

FIGS. 4 through 7 show a first preferred embodiment of sequence valve 18. FIG. 4 shows valve 18 in its normal initial operating position for piggyback operation. As shown in FIG. 4, tubes 30 and 40 pass side-by-side through valve 18. At the upper end, tubing 30 and tubing 40 are retained by retainer spring 102, which has a pair of retainer arms 102A and 102B. At the lower end, tubing 30 and tubing 40 are retained in side-by-side position by retaining figures 104A and 104B of front cover 106.

As shown in FIG. 4, lever 100 is in its uppermost ("cocked") position, which causes occluder stud 108 to be in its leftmost position. As a result, primary tubing 30 is pinched off between occluder stud 108 and leaf spring 110. Also shown in phantom in FIG. 4 is the position of lever 100 and the position of occluder stud 108 after sequence valve 18 has received a valve control signal from pump 12 which causes occluder stud 108 to move generally to the right to pinch off secondary tubing 40 between occluder stud 108 and wall 112. Thus sequence valve 18 has two stable positions, one in which primary tubing 30 is occluded and secondary tubing 40 is unoccluded; and the other in which secondary tubing 40 is occluded and primary tubing 30 is unoccluded.

FIG. 5 shows sequence valve 18 with front cover 106 removed. The operating mechanisms of sequence valve 18 are supported by valve base 114. Both occluder stud 108 and lever 100 are attached to bell crank 116, which is pivotally mounted to valve base 114 by pivot pin 118.

As in FIG. 4, two positions of occluder stud 108 and the other moving parts of sequence valve 18 are shown. Solid lines represent the initial position in which primary tubing 30 is occluded, and phantom lines illustrate the second position in which secondary tubing 40 is occluded.

Bell crank 116 is biased in a clockwise direction by bias spring 120, which is connected at its upper end to stud 12 and thus to valve base 114, and which is connected to its lower end to stud 124 which projects rearwardly from the lower end of bell crank 118.

Latch 126 is pivotally mounted about pivot pin 128, and has a latch tooth 130 which engages lower leg 132 of bell crank 116 when lever 100 is in its cocked upper position. Latch arm 134 is held in the initial position by solenoid plunger 136, which prevents rotation of latch 126 about the axis defined by pivot pin 128.

Valve 18 will remain in a stable initial position until a valve control signal actuates solenoid 138 (FIG. 6). This causes solenoid plunger 136 to be pulled in a rearward direction out of contact with arm 134 of latch 126. This allows the bias force of spring 120 to rotate bell crank 116 and in turn latch 126 about their respective pivot points 118 and 128 to the position shown in phantom in FIG. 5. In the second stable position of bell crank 116, leg 132 of bell crank 116 is located near stop 140 (which limits rotation of bell crank 116 if secondary tubing 40 is not in position to be pinched off). In this second stable state, occluder stud 108 is near its rightmost position, so that secondary tubing 40 is pinched off between occluder stud 108 and wall 112.

Sequence valve 18 is reset to its initial position by moving lever 100 upward to the initial cocked position shown in solid lines. Latch spring 142 urges latch 126 back to its initial position when sequence valve 18 is being reinitialized. As shown in FIG. 6, rear surface 134A of arm 134 is bevelled to form a ramp which allows arm 134 to move past solenoid plunger 136 as lever 100 is being cocked.

Solenoid 138 includes a solenoid plunger stud 144 which extends out of the rear end of solenoid cover 146. At the rear end of solenoid plunger stud 144 is solenoid button 148. This button allows the nurse or technician to pull solenoid plunger 136 out of the way of latch 126 in order to manually release lever 100, bell crank 116 and latch 126 from the cocked position. Button 148 can then be released and, due to the bias force of bias spring 150, solenoid plunger 136 returns to its normal position shown in FIG. 6.

It is also preferable for sequence valve 18 to provide an electrical signal which indicates the current state of sequence valve 18. In the embodiment shown in FIG. 5, a metal contact stud 152 is attached to bell crank 116. When valve 18 is in its initial state, contact stud 152 is in contact with contact wire 154. When the valve control signal has been received and bell crank 116 has rotated to the position shown in phantom, contact stud 152 has moved into engagement with contact wire 156. Depending upon which wire 154 or 156 is in contact with contact stud 152, a different electrical signal is supplied through cable 52 to pump 12. This provides a simple, yet very effective way of indicating the state of sequence valve 18 to pump 12.

As shown in FIG. 7, upper retainer 102 is a single wire clip which mounts over stud 158 at the upper end of valve base 114. The resilient nature of retainer 102 allows the retainer arms 102A and 102B to be displaced outwardly while tubing 30 and 40 are inserted into sequence valve 18. Once released, arms 102A and 102B return to their normal position shown in FIG. 7, thus securely holding tubing 30 and tubing 40 in place.

Sequence valve 18 shown in FIGS. 4–7 is particularly advantageous, since it is small, light-weight (so that it can be supported on tubing 30 and 40 without the need for a separate support stand) and uses a small, low-power solenoid. By using a pivoted latch 126 and a pivoted bell crank 166, both of which provide a substantial mechanical advantage (e.g. 4:1 each), a very small movement of solenoid plunger 136 provides the sufficient force to move occluder stud 180 to the right so as to pinch off tubing 40. The force required to move solenoid plunger 136 is only that necessary to overcome frictional force between latch 126 and solenoid plunger 136. This frictional force is greatly reduced due to the mechanical advantage provided by crank 116 and latch 126.

Sequence valve 18 shown in FIGS. 4–7 also uses an extremely simple mechanism to pinch off alternately either tubing 30 or tubing 40. By the use of leaf spring 110 to urge tubing 30 toward occluder stud 108, sequence valve 18 does not require a precise alignment of both positions of occluder stud 108, and variations in the diameters of tubing 30 and 40 are accommodated. It is merely necessary to ensure that occluder stud 108 moves far enough to the right to pinch off tubing 40 against the right wall 112 for the minimum expected diameter of tubing 40.

FIGS. 8–12 show a second embodiment of the sequence valve of the present invention. This second embodiment (which is designated valve 18') is generally similar to the embodiment of sequence valve 18 shown in FIGS. 4–7, and similar reference numerals are used to designate similar elements. The internal operation of the bell crank, latch and solenoid of sequence valve 18' of FIGS. 8–12 are identical to those shown in FIGS. 4–7 and will not be discussed again.

Figure 8:
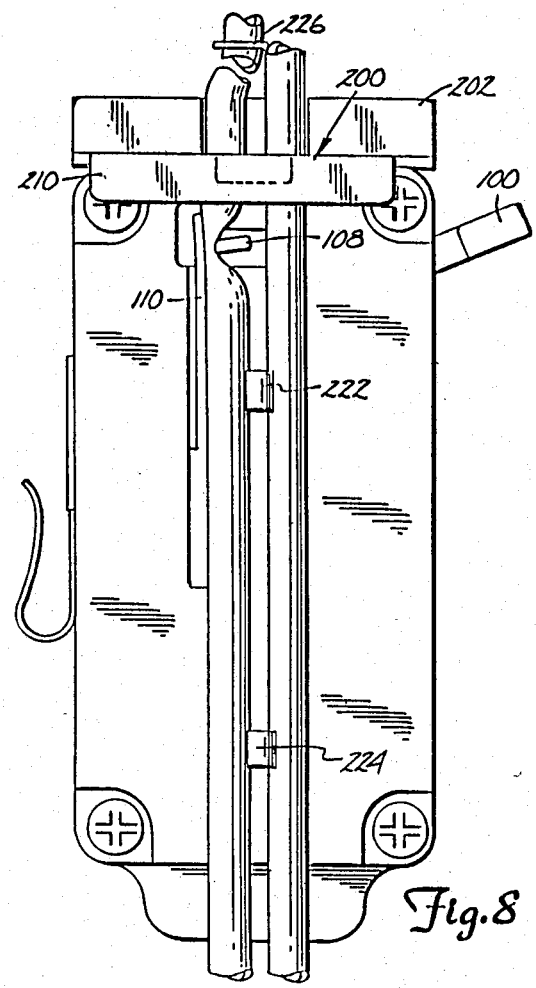
FIG. 8 is a front view of a second preferred embodiment of the sequence valve.
Figure 9:
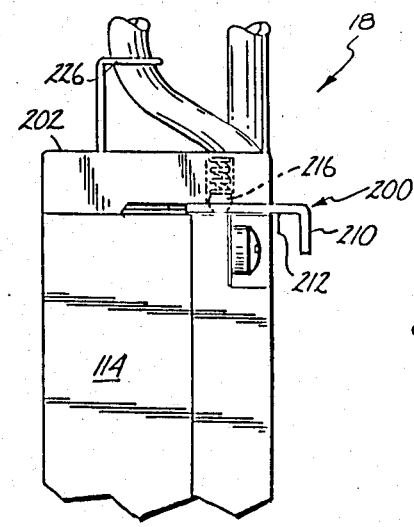

The main difference between sequence valve 18' of FIGS. 8–12 and sequence valve 18 of FIGS. 4–7 is in the retaining of tubing 30 and 40. In sequence valve 18', a tube retainer 200 is pivotally mounted at the upper end of valve 18' between top end plate 202 and the upper ends of front cover 106 and valve base 114. Tube retainer 200 has a right leg 204 which is pivotally mounted about pivot pin 206, a left leg 208, a front flange 210, and a tube hold-down flange 212. The closed position of tube retainer 200 is shown in FIGS. 8–10, and the open position is shown in FIG. 11. Flange 210 forms a handle by which the nurse can pivot tube retainer 200 to the open position to allow insertion or removal of tubing 30 and 40 from sequence valve 18'.

Left leg 208 of tube retainer 200 contains a hole 214 which receives a spring loaded ball 216 mounted on top plate 202 when tube retainer 200 is in the closed position shown in FIGS. 8–10. Spring loaded ball 216 maintains tube retainer 200 in the closed position and prevents it from moving from the closed position if IV pump 12 or tubing 30 or 40 are moved or bumped inadvertently.

Sequence valve 18' also uses tube retainer 200 as a switch to indicate to pump 12 that sequence valve 18' is in a condition to operate. For this purpose, tube retainer 200 is an electrically conductive material, preferably metal. An electrically conductive washer 218, which is partially shown in FIG. 11, is mounted on pivot pin 206 in contact with right leg 204 of tube retainer 200. Spring contact 200 is positioned so that it will be engaged by left leg 208 when tube retainer 200 is in the closed position. Thus when tube retainer 200 is in the closed position, a closed electrical path is provided between conductive washer 218 and spring contact 220.

FIG. 12 shows an electrical schematic diagram of sequence valve 18'. In this embodiment, cable 52 (which connects valve 18' to pump control 94) contains four wires 52A, 52B, 52C and 52D. Solenoid 138 is connected between wires 52A and 52B. Wire 52B is connected to ground. When pump control 94 causes a voltage to be present between wires 52A and 52B, solenoid 138 is actuated.

Wires 52C and 52D are used to indicate to pump control 94 the condition or state of sequence valve 18'. The switch formed by tube retainer 200, conductive washer 218 and spring contact 220 is connected in series with a switch formed by contact stud 152 and contact wires 154 and 156. Contact wire 154 is connected to wire 52D, and contact wire 156 is connected to wire 52C.

If tube retainer 200 is in its open position, both wires 52C and 52D will indicate an open circuit. When tube retainer 200 is closed, normally one of the two wires 52C and 52D will be an open circuit, while the other will be connected to ground. By monitoring wires 52C and 52D, therefore, pump control 94 can determine the operating state of sequence valve 18', as well as whether tube retainer 200 is in its closed position.

FIGS. 8–11 also show retainer posts 222 and 224, which are positioned along the channel, and which maintain tubing 30 and 40 in position along the entire length of the channel.

At the upper end of valve 18' is hook 226, which is attached by screw 228 to top plate 202. Primay tubing 30 is threaded through hook 226 to maintain sequence valve 18' in a generally vertical position. This counteracts the tendency of the lower end of valve 18' to tip forward due to the greater weight of solenoid 138 within solenoid housing 146 (see FIG. 6).

Also included in sequence valve 18' is a spring clip 230 and retainer pad 232 which are positioned along the left side of sequence valve 18'. Clip 230 allows sequence valve 18' to be clipped onto pump 12 when not in use. Pad 232 prevents sequence valve 18' from slipping when it is clipped onto pump 12.

FIGS. 13A–19C show a third embodiment of the sequence valve of the present invention. This third embodiment (which is designed valve 18") is generally similar to sequence valves 18 and 18' which have been discussed previously. Similar reference numerals are used to designate similar elements. Except as specifically discussed, the operation of sequence valve 18" is generally similar to the operation of valves 18 and 18', and not all elements of valve 18" will be discussed in detail for that reason.

With the present invention, it is possible to provide multiple doses of the piggyback or secondary solution within secondary container 16. Typically, the secondary medication is intended to be provided to the patient only in limited doses. Although secondary container 16 may contain four or even six doses, it is important that a patient will not receive multiple doses at one time due to malfunction or improper setup. The third embodiment of the present invention includes several features which are specifically directed to preventing a dangerous situation in which multiple doses of the secondary solution are provided to the patient at one time.

First, valve 18" includes features to prevent the nurse from reversing primary tubing 30 and secondary tubing 40.

Second, sequence valve 18" is provided with several sensing mechanisms for ensuring that the secondary tubing 40 is in position within sequence valve 18 and is occluded when the sequence valve 18" switches state.

Third, sequence valve 18" also determines that bell crank 116 has moved with a sufficient momentum to pinch off secondary tubing 40 when sequence valve 18" changes state.

To prevent reversal of the primary and secondary tubing 30 and 40, sequence valve 18 requires that tubing 30 and 40 be of different outer diameters. Preferably, primary tubing 30 has a greater outer diameter than secondary tubing 40. In one embodiment, the outside diameter of primary tubing 30 is 0.160 inches and the outer diameter of secondary tubing 40 is 0.125 inches.

As shown in FIGS. 13A–13D, 14A–14D and 15A–15D, sequence valve 18" has a main channel 240 formed in front cover 106 and top end cover 202 which is divided into parallel primary and secondary channels 240A and 240B, respectively, which are of different size. At the upper end of channel 240, semi-circular grooves 241 and 242 in top end plate 202 and front plate 106, respectively, define the upper end of primary channel 240A. Secondary channel 240B is defined at the upper end of sequence valve 18" by semi-circular groove 243 in end cover 202 and semi-circular grooves 224 and 246 in front cover 106. Grooves 241 and 243 are separated from one another by rib 248 of end plate 202, and grooves 242 and 244 are separated by rib 250 of front plate 106. Below the occluder stud position, rib 252 separates groove 246 from primary channel 240A. Near the bottom end of channel 240, retainer post 224 separates primary and secondary channels 240A and 240B. Shoulder 254 is positioned opposite retainer post 224 to narrow the width of secondary channel 240B.

When primary tube 30 is in position in primary channel 240A, it is covered and held in position by control gate 256. At its lower end, control gate 256 is pivotally connected to front plate 106 by screw 258 (see FIGS. 14B and 17) so that it pivots about axis 260 (see FIG. 16).

Control gate 256 has an upper arm 262 and a lower arm 264 for covering the front side of primary channel 240A when control gate 256 is closed. Upper arm 262 covers groove 242 between rib 250 and rib 266. Lower arm 264 covers the portion of primary channel 240A between rib 252 and leaf spring 110. Lower arm 264 has a first section 264A which is curved to avoid interference with leaf spring 110, and a second section 264B which engages rib 252 and covers primary channel 240A.

Control gate 256 also includes a handle 268 to permit the operator to move control gate 256 between its open and closed positions. As will be discussed in further detail in conjunction with FIGS. 16–18, control gate 256 also includes a leg 270 which has a notch 272. Leg 270 and notch 272 cooperate with tooth 274 of bell crank 116 to ensure proper positioning of primary tube 30 and control gate 256 when lever 100 is cocked.

Tube retainer 200 includes an integral tube retainer insert 276 which is attached (such as by soldering) to the rear and bottom surfaces of tube retainer 200. Retainer insert 276 has a first semi-circular section 278 which covers groove 244, a second semi-circular section 280 which covers a portion of groove 246, and a third semi-circular section 282 which covers a portion of primary channel 240A between lower arm 264 of control gate 256 and occluder stud 108.

When tube retainer 200 is closed, therefore, it overlies the upper ends of primary and secondary channels 240A and 240B, as well as control gate 256 to cause the upper ends of primary and secondary channels 240A and 240B to be passageways of circular cross-section.

Figure 14A:
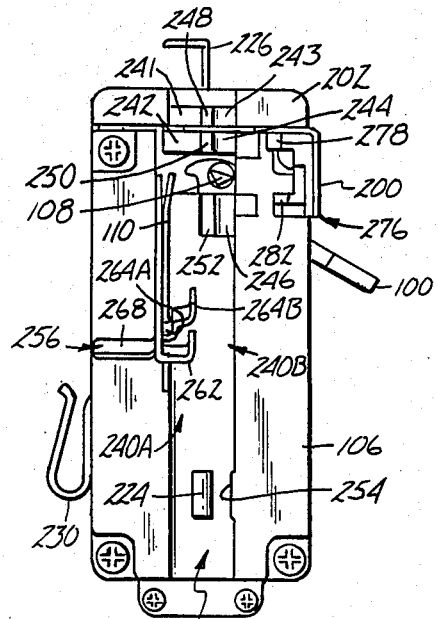
FIGS. 14A–14D are front views, similar to FIGS. 13A–13D, respectively, of the sequence valve.

FIGS. 13A, 14A and 15A show the first step in the process of setting up sequence valve 18" for operation. In these three figures, both tube retainer 200 and control gate 256 are open and neither primary tube 30 nor secondary tube 40 have yet been inserted. Lever 100 is in its lowermost position, and occluder stud 108 is in its rightmost position.

Figure 14B:
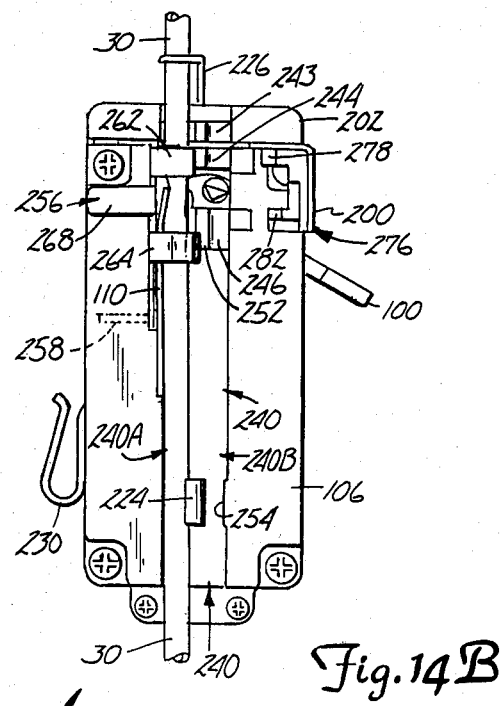

In FIGS. 13B, 14B and 15B, primary tube 30 has been inserted and control gate 256 has been closed. Tube retainer 200 remains open at this point in the setup procedure.

Figure 14C:
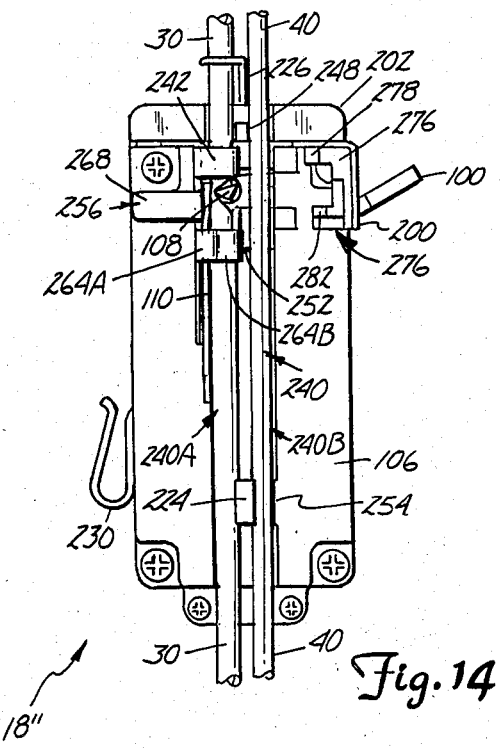

In FIGS. 13C, 14C and 15C lever 100 has been cocked so that it is in its uppermost position and occluder stud 108 has moved to its leftmost position. As a result, primary tube 30 is pinched off between occluder stud 108 and leaf spring 110. Secondary tubing 40 is then inserted in channel 240B.

Figure 14D:
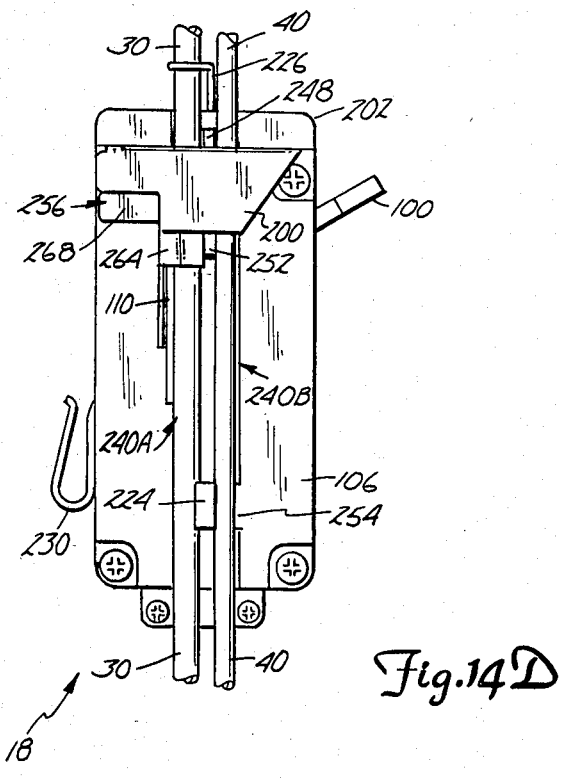

In FIGS. 13D, 14D and 15D, tube retainer 200 has been closed. At this point, sequence valve 18" is ready to begin operation.

Because of the difference in size of primary channel 240A and secondary channel 240B, it is not possible to reverse the positions of primary tubing 30 and secondary tubing 40. Although secondary tubing 40 could be placed all primary channel 240A, primary tubing 30 is too large to fit in secondary channel 240B. This will become immediately apparent to the nurse, who will be unable to insert primary tubing 30 into secondary channel 240B, and will be unable to close tube retainer 200. The use of two different sized channels 240A and 240B, therefore, provides a simple, yet extremely effective, method for preventing an erroneous reversal of the primary tubing 30 and secondary tubing 40 within valve 18".

FIGS. 16-18 illustrate the interaction of bell crank 116 and control gate 256. Leg 270 of control gate 256 travels along a path which intersects the path of tooth 274 of bell crank 116. As a result, if control gate 256 is open and lever 100 is cocked to its uppermost position, tooth 274 is in its leftmost position which blocks the path of leg 270. As a result, control gate 256 cannot be closed if lever 100 has been cocked first. If control gate 256 cannot be closed, tube retainer 200 also cannot be closed because control gate 256 is in the way. This is a clear indication to the nurse who is setting up sequence valve 18" that the proper setup sequence has not been followed. In addition, the switch formed by tube retainer 200 is not closed, and pump 10 will not operate. The nurse must then pull on solenoid release knob 148 to release bell crank 116 and start the setup sequence again.

If control gate 256 is only partially closed and the nurse attempts to cock lever 100, leg 270 will be positioned in the path of tooth 274. Thus it will not be possible to cock lever 100 when control gate 256 is partially closed.

The proper time for cocking lever 100 is when primary tube 30 is in primary channel 240A and control gate 256 is closed. Under those conditions, notch 272 is aligned with the path of tooth 274, so that bell crank 116 can pivot to the cocked position shown in FIG. 18. In this position, tooth 274 projects through notch 272, thus preventing control gate 256 from being opened as long as lever 100 is cocked. This prevents any inadvertent or deliberate attempt to remove primary tube 30 from primary channel 240A as long as lever 100 is cocked.

During setup of an IV administration system, it is common for some of the IV fluid to be spilled. The primary solution generally is a glucose solution, which when it dries is sticky and can interfere with the proper operation of moving parts. Of particular concern is the proper movement of bell crank 116 and occluder stud 108 so that secondary tubing 40 is pinched off when the valve changes state. This is of critical importance, since incomplete occlusion could allow an overdose of the secondary fluid to be pumped to the patient, with potentially dangerous results.

Figure 19A:
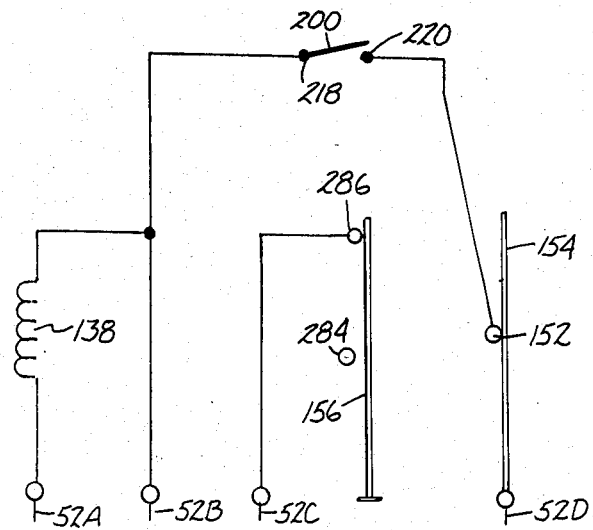
FIGS. 19A–19C are electrical schematic diagrams illustrating operation of the sensing of bell crank position and presence of the secondary tubing in the sequence valve.
Figure 19B:
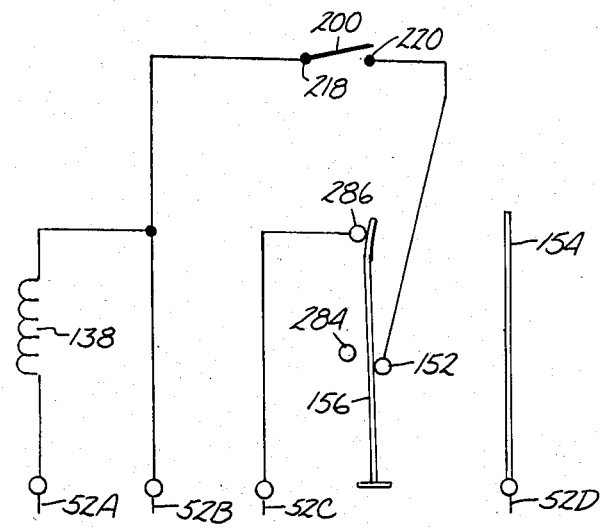
Figure 19C:
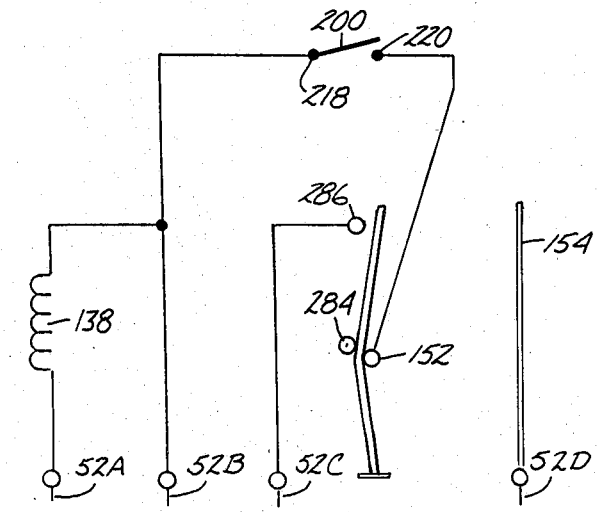

In a preferred embodiment of the present invention shown in FIGS. 19A-19C, contact wires 54 and 56 are provided to indicate the position of bell crank 116. The circuit shown schematically in FIGS. 19A-19C is generally similar to the circuit shown in FIG. 5, and similar reference characters are used to designate similar elements. Contact stud 152 is provided on bell crank 116 for contacting contact wires 154 and 156. When lever 100 is in its cocked position, contact stud 152 is in contact with wire 154 as shown in FIG. 19A. When valve 18" is actuated, bell crank 116 moves toward its uncocked position, and contact stud 152 contacts wire 156 (FIG. 19B).

Occluder stud 108 will contact secondary tubing 40 before bell crank 116 reaches its fully uncocked position. In one embodiment, the distance from the occluder stud 108 to the right wall of secondary channel 240B is 0.053 inches when the occluder stud contact 152 makes contact with wire 156. The rest position of occluder stud 108 to the right wall of secondary channel 240B which produces occlusion of tubing 40 is 0.033 inches. If no tube is present in secondary channel 240B, the distance from the occluder stud 108 to the right wall of the secondary channel 240B is 0.010 inches.

In a preferred embodiment of the present invention, contact wire 156 is positioned to sense when bell crank 116 has reached a point where occluder stud 108 begins to contact secondary tubing 40. This does not, however, provide an absolute indication that bell crank 116 is moving with sufficient force to be able to fully occlude secondary tubing 40. For example, if the sequence valve 18" has become exposed to glucose solution, bell crank 116 may be moving so slowly that it does not have sufficient momentum to carry it through to final position which fully occludes secondary tubing 40. To detect this potential error condition, pump control 94 (FIG. 3) senses the time from when contact stud 152 breaks contact with contact wire 154 until it makes contact with contact wire 156. If that measured time is less than a predetermined value, it indicates that the bell crank 116 is moving with sufficient velocity and has sufficient momentum to fully occlude tubing 40. If, on the other hand, contact is never made with contact wire 156, or the time interval is greater than the predetermined value, an alarm is provided, since this indicates that bell crank 116 may not have sufficient momentum to occlude secondary tubing 40.

As shown in FIGS. 19A-19C, contact wire 156 is fixed at one end and free at its opposite end. If secondary tubing 40 is not in channel 240B, contact stud 152 applies force to contact wire 156 which bends contact wire 156 around fixed post 284 (FIG. 19C). This causes the free end of contact wire 156 to break contact with terminal 286. As a result, the signal on wire 52C will go from high (FIG. 19A) to low (FIG. 19B) to high (FIG. 19C) if secondary tubing 40 is not in channel 240B. By monitoring the signal transitions on lines 52C and 52D, therefore, pump control 94 can determine the existence of a potential error condition and provide an alarm through annunciator 90.

FIG. 20 shows still another improvement to the sequence valve 18" of the present invention. In this modified embodiment, a second leaf spring 288 is located along the right hand side of secondary channel 240B. Leaf spring 288 cooperates with occluder stud 108 to pinch off secondary tubing 40 when valve 18" is actuated. Leaf spring 288 provides a greater amount of tolerance in positioning, and also allows a slight amount of "give" as occluder stud 108 moves toward secondary tubing 40.

Leaf spring 288 allows contact wire 156 to be positioned at the point where occlusion of secondary tubing 40 normally takes place. Spring 288 is stiff enough to allow secondary tubing 40 to be pinched off between occluder stud 108 and spring 288, yet allows a slight amount of over-travel of occluder stud 108 beyond the point at which occlusion first occurs. As a result, contact wire 156 can be positioned at the point where occlusion initially takes place, with assurance that occluder stud 108 will actually move slightly past that position.

In contrast, when the right hand side of secondary channel 240B is fixed (as in the other embodiments of the present invention), contact wire 156 must be placed at a position slightly before occlusion normally takes place. Otherwise, a slight variation in wall thickness or other dimension of the secondary tubing 40 can result in a failure of contact stud 152 to make contact with contact wire 156 and thus cause a nuisance alarm.

Although the present invention has been described with reference to preferred embodiments, workers skilled in the art will recognize that changes may be made in form and detail without departing from the spirit and scope of the invention. For example, although the present invention has been described in the context of a system in which a primary and only one secondary bag are used, it is also applicable to more complex systems in which multiple secondary bags are used in conjunction with a primary bag.

Similarly, although the present invention has been described in the context of a specific type of IV pump, the present invention is applicable to other IV pump and controller systems as well.

What is claimed is:

1. A sequence valve for selectively occluding first and second flexible tubes in sequence, the sequence valve comprising:
   a base;
   a crank pivotally connected to the base for movement between first and second crank positions;
   bias means for providing a bias force to the crank which urges the crank toward the second crank position;
   occluder means connected to the crank for occluding the first flexible tube when the crank is in the first crank position, and for occluding the second flexible tube when the crank is in the second crank position;
   releasable latch means for latching the crank in the first crank position and for releasing the crank in response to a control signal to allow the bias force to pivot the crank to the second crank position; and
   means for sensing a condition indicative of failure of the sequence valve to occlude the second flexible tube and providing a signal in response thereto.

2. The sequence valve of claim 1 wherein the means for sensing a condition comprises:
   contact means for contacting a first switch element when the crank is in the first crank position and for contacting a second switch element when the crank is in the second crank position to provide signals representative of the position of the crank.

3. The sequence valve of claim 2 wherein the means for sensing a condition further comprises:
   means for measuring a time from when the contact means breaks contact with the first switch element until the contact means makes contact with the second switch element.

4. The sequence valve of claim 3 and further comprising:
   means for providing an alarm signal if the time measured is greater than a predetermined value.

5. The sequence valve of claim 2 wherein the crank is movable to third position past the second crank position if the occluder means does not engage the second flexible tube, and wherein the means for sensing a condition further comprises:
   means for causing the contact means and the second switch element to break electrical contact if the crank moves to third position.

6. The sequence valve of claim 5 wherein the second switch element comprises a contact wire having a fixed end and a free end, and a terminal normally in contact with the free end; and wherein the means for causing the contact means and the second switch element to break electrical contact engages and deflects the contact wire when the crank moves to the third position to cause the free end to move out of contact with the terminal.

7. The sequence valve of claim 1 wherein the means for sensing a condition comprises:
   means for sensing when the crank has moved to a third position which can only be reached if the second flexible tube is not in position to be occluded by the occluder.

8. The sequence valve of claim 1 wherein the means for sensing a condition comprises:
   means for sensing rate of movement of the crank from the first crank position toward the second crank position.

9. The sequence valve of claim 1 and further comprising:
   channel means for positioning the first and second tubes in side-by-side relationship.

10. The sequence valve of claim 9 wherein the occluder means comprises an occluder stud connected to the crank and extending into the channel means between the first and second tubes so that when the crank is in the first crank position the occluder stud causes the first tube to be pinched off and when the crank is in the second crank position the occluder stud causes the second tube to be pinched off.

11. The sequence valve of claim 10 and further comprising:
    a first leaf spring on one side of the channel means for urging one of the tubes toward the occluder stud.

12. The sequence valve of claim 11 and further comprising:
    a second leaf spring on an opposite side of the channel means for urging the other of the tubes toward the occluder stud.

13. A sequence valve for selectively occluding first and second flexible tubes in sequence, the sequence valve comprising:
    spring biased pivotable tube pincher means for pinching off the first and then the second flexible tube;
    pivotable latch means for holding the tube pincher in a position in which the first tube is pinched off;
    a solenoid means which releases the latch in response to a control signal to permit the latch to pivot out of engagement with the tube pincher and thereby allow the tube pincher to pivot to a position in which the second tube is pinched off; and
    means for sensing a condition indicative of a failure of the tube pincher to pinch off the second tube and providing a signal in response thereto.

14. The sequence valve of claim 13 wherein the means for sensing a condition comprises:
    means for sensing when the tube pincher has moved to a position which can only be reached if the second flexible tube is not in position to be pinched off by the tube pincher.

15. The sequence valve of claim 13 wherein the means for sensing a condition comprises:
    means for sensing rate of movement of the tube pincher from the position in which the first tube is pinched off toward the position in which the second tube in pinched off.

16. An IV administration system comprising:
    a first source of a first IV fluid;

a second source of a second IV fluid;
an IV control device having an inlet and an outlet for delivering IV fluids;
a first flexible tube connected between the first source and the inlet;
a second flexible tube connected between the second source and the inlet;
a sequence valve for switching, in response to a control signal, from a first state in which the first flexible tube is occluded and the second flexible tube is not to a second state in which the second flexible tube is occluded and the first flexible tube is not;
means for providing the control signal to the sequence valve; and
means for sensing a condition indicative of failure of the sequence valve to occlude the second flexible tube in response to the control signal and providing a signal in response thereto.

17. The system of claim 16 wherein the sequence valve comprises:
a base;
a crank pivotally connected to the base for movement between first and second crank positions;
bias means for providing a bias force to the crank which urges the crank toward the second crank position;
occluder means connected to the crank for occluding the first flexible tube when the crank is in the first crank position, and for occluding the second flexible tube when the crank is in the second crank position; and
releasable latch means for latching the crank in the first crank position and for releasing the crank in response to a control signal to allow the bias force to pivot the crank to the second crank position.

18. The system valve of claim 17 wherein the means for sensing a condition comprises:
means for sensing when the crank has moved to a position which can only be reached if the second flexible tube is not in position to be occluded by the occluder means.

19. The system of claim 17 wherein the means for sensing a condition comprises:
means for sensing rate of movement of the crank from the position in which the first tube is pinched off toward the position in which the second tube is pinched off and providing a signal in response thereto.

20. The system of claim 16 wherein the sequence valve comprises:
a spring biased pivotable tube pincher for pinching off the first and then the second tube;
a pivotable latch for holding the tube pincher in a position in which the first tube is pinched off; and
a solenoid which releases the latch in response to a control signal to permit the latch to pivot out of engagement with the tube pincher and thereby allow the tube pincher to pivot to a position in which the second tube is pinched off.

21. The system of claim 20 wherein the means for sensing a condition comprises:
means for sensing when the tube pincher has moved to a position which can only be reached if the second flexible tube is not in position to be occluded by the occluder means.

22. The system of claim 20 wherein the means for sensing a condition comprises:
means for sensing rate of movement of the tube pincher from the position in which the first pincher is pinched off toward the position in which the second tube is pinched off and providing a signal in response thereto.

23. An IV administration system comprising:
a first source of a first IV fluid;
a second source of a second IV fluid;
an IV control device having an inlet and an outlet for delivering IV fluids;
a first flexible tube connected between the first source and the inlet;
a second flexible tube connected between the second source and the inlet;
a sequence valve for initially occluding the first flexible tube and then occluding the second flexible tube in response to a control signal;
means for providing the control signal to the sequence valve; and
means for sensing a condition indicative of failure of the sequence valve to occlude the second tube in response to the control signal and providing a signal in response thereto.

24. The system of claim 23 wherein the sequence valve includes a movable occluder which is actuated in response to the control signal.

25. The system of claim 24 wherein the means for sensing a condition senses a rate of movement of the occluder and providing a signal in response thereto.

26. The system of claim 24 wherein the means for sensing a condition senses movement of the occluder to a position which is only possible if the second tube is not in position to be occluded.

27. The system of claim 23 wherein the means for sensing a condition senses absence of the second tube from the sequence valve.

* * * * *